(12) United States Patent
Ito

(10) Patent No.: US 7,651,255 B2
(45) Date of Patent: Jan. 26, 2010

(54) LIGHT SOURCE APPARATUS FOR ELECTRONIC ENDOSCOPE AND ELECTRONIC ENDOSCOPE HAVING THE LIGHT SOURCE APPARATUS

(75) Inventor: Shunichi Ito, Tokyo (JP)

(73) Assignee: Hoya Corporation, Tokyo (JP)

( * ) Notice: Subject to any disclaimer, the term of this patent is extended or adjusted under 35 U.S.C. 154(b) by 768 days.

(21) Appl. No.: 11/423,478

(22) Filed: Jun. 12, 2006

(65) Prior Publication Data

US 2006/0287581 A1 Dec. 21, 2006

(30) Foreign Application Priority Data

Jun. 16, 2005 (JP) ............... 2005-176098

(51) Int. Cl.
*A61B 1/06* (2006.01)
*F16H 3/72* (2006.01)

(52) U.S. Cl. ................ 362/574; 600/178; 600/180; 475/5; 475/282

(58) Field of Classification Search ............... 600/178, 600/180; 362/574; 475/5, 282, 311, 317
See application file for complete search history.

(56) References Cited

U.S. PATENT DOCUMENTS

| | | | | |
|---|---|---|---|---|
| 4,729,018 A | * | 3/1988 | Watanabe et al. | 348/69 |
| 4,740,837 A | | 4/1988 | Yanagisawa et al. | |
| 4,971,435 A | * | 11/1990 | Shaw et al. | 352/59 |
| 5,042,915 A | * | 8/1991 | Akutsu et al. | 359/230 |
| 6,334,845 B1 | * | 1/2002 | Higuchi et al. | 600/181 |
| 6,413,211 B2 | * | 7/2002 | Higuchi et al. | 600/181 |
| 6,817,977 B2 | | 11/2004 | Ito | |
| 6,974,240 B2 | * | 12/2005 | Takahashi | 362/574 |
| 2004/0209722 A1 | * | 10/2004 | Ai | 475/5 |
| 2005/0220447 A1 | | 10/2005 | Ito | |
| 2006/0052214 A1 | | 3/2006 | Ito | |
| 2006/0088303 A1 | | 4/2006 | Ito | |

FOREIGN PATENT DOCUMENTS

| | | |
|---|---|---|
| JP | 62-69222 | 3/1987 |
| JP | 7-85132 | 9/1995 |
| JP | 2006-102474 | 4/2006 |
| JP | 2006-116189 | 5/2006 |
| JP | 2006-116190 | 5/2006 |

* cited by examiner

*Primary Examiner*—John P Leubecker
(74) *Attorney, Agent, or Firm*—Greenblum & Bernstein P.L.C.

(57) ABSTRACT

A light source apparatus for an electronic endoscope includes a light source; a rotary shutter including a pair of aperture controlling rotary plates; a first planetary gear mechanism including a first internal tooth gear, a first sun gear rotated with one aperture controlling rotary plate, and a first planet gear engaged with the first internal tooth gear and the first sun gear; a second planetary gear mechanism including a second internal tooth gear, a second sun gear rotated with the other aperture controlling rotary plate, and a second planet gear engaged with the second internal tooth gear and the second sun gear; and a carrier device which holds the first and second planet gears. An endless timing belt is installed on an output gear of a phase-difference motor and an input tooth portion of the second internal tooth gear, and includes a meshing portion.

5 Claims, 9 Drawing Sheets

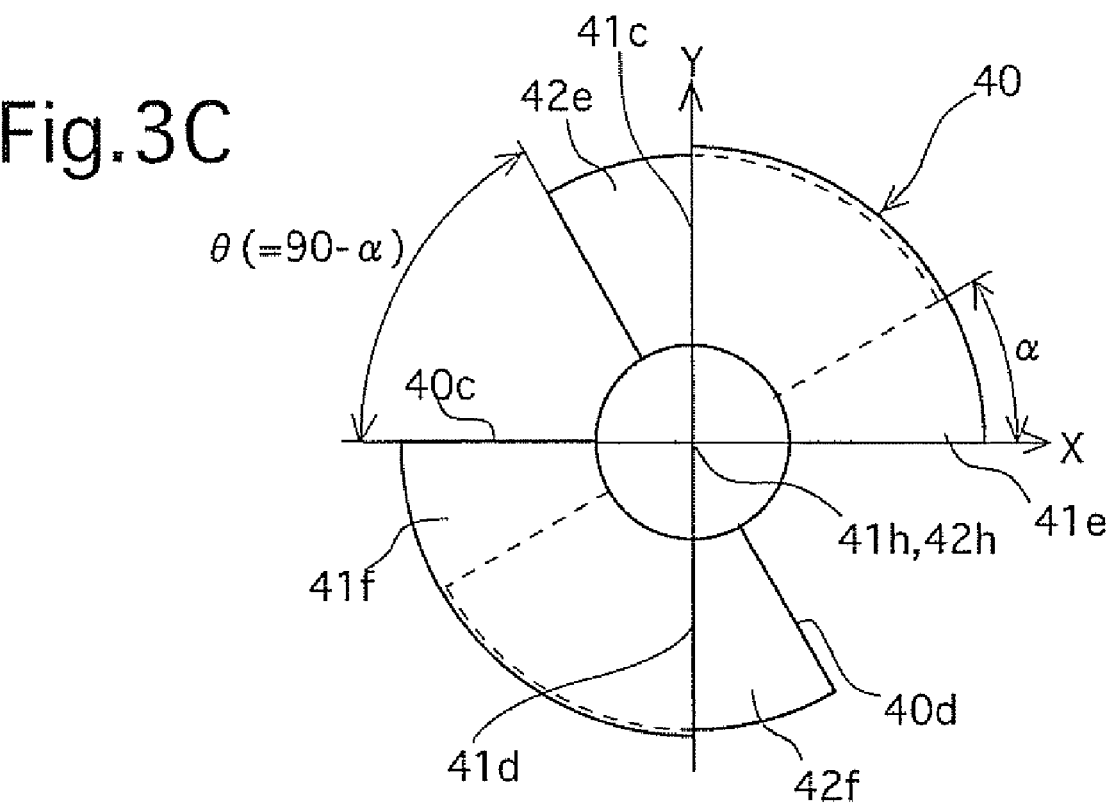

LIGHT SOURCE APPARATUS FOR ELECTRONIC ENDOSCOPE AND ELECTRONIC ENDOSCOPE HAVING THE LIGHT SOURCE APPARATUS

BACKGROUND OF THE INVENTION

1. Field of the Invention

The present invention relates to an electronic endoscope, and more specifically relates to a light source apparatus for an electronic endoscope using a plurality of aperture controlling rotary plates.

2. Description of the Prior Art

In conventional electronic endoscopes, in order to provide appropriate light modulation, an endoscope recording apparatus has been proposed in, for example, U.S. Pat. No. 4,729,018 (based on Japanese Unexamined Patent Publication No. 62-69222). The apparatus disclosed in this publication is provided with a rotary shutter having a rotatable shaft, wherein the distance between the axis of the rotatable shaft and the optical axis of illuminating light emitted from a light source for the endoscope is variable. The rotary shutter is shaped so that a difference in peripheral speed occurs between the radial portions thereof, i.e., the rotary shutter is shaped so that the aperture size varies during rotation of the rotary shutter. Light modulation is carried out by altering the distance between the axis of the rotatable shaft and the optical axis of illuminating light and by utilizing the peripheral speed difference of the rotary shutter.

In Japanese Unexamined Patent Publication No. 62-69222, light modulation can be performed, however, the structure of the rotary shutter is complex. Furthermore, it is necessary to provide a mechanism to vary the distance between the rotary shutter and the optical axis of the light source for the endoscope. Accordingly, the manufacturing cost is high and the manufacturing process is troublesome. Moreover, in order to achieve such a construction, the outer diameter of the rotary shutter must be several times larger than that of the light bundle, thus resulting in an increase in size of the rotary shutter. If the rotary shutter is asymmetrical in shape with respect to the rotation axis thereof in order to vary the aperture, the center of rotation does not align with the center of gravity, so that the rotary shutter tends to lose balance during rotation. Consequently, correct emission of the illuminating light cannot occur, and the rotary shutter and the surrounding members may break.

Upon considering the above-mentioned problems, the applicant of the present invention has proposed a light source apparatus for an electronic endoscope including a light source; a rotary shutter for intercepting or transmitting light emitted from the light source toward a light guide, the rotary shutter including a pair of aperture controlling rotary plates having axes coaxial with each other and extending parallel with an optical axis of the light source. The aperture controlling rotary plates can be rotated together (integrally) with each other and each includes light interception portions and opening portions alternately arranged in a rotation direction, wherein a combined opening angle of the opening portions of the rotary shutter is varied by a relative rotation of the pair of aperture controlling rotary plates (Japanese Unexamined Patent Publication No. 2006-102474).

The invention disclosed in Japanese Patent Application No. 2005-26568 discloses a light source apparatus for an electronic endoscope including a pair of planetary gear mechanisms which are driven by a phase difference motor, provided separate from a chopper motor, and furthermore, the pair of planetary gear mechanisms are associatively connected to a pair of aperture controlling rotary plates, respectively. Accordingly, when only the chopper motor is driven, the pair of aperture controlling rotary plates rotate at the same rotational speed so that the aperture angle of the aperture remains unchanged. On the other hand, if both the chopper motor and the phase difference motor are driven, a difference in rotational speed between the pair of aperture controlling rotary plates occurs, so that the pair of aperture controlling rotary plates rotate while changing the aperture angle of the aperture.

In the invention disclosed in Japanese Patent Application No. 2005-26568, since the output gear of the phase difference motor and the input gear of the planetary gear mechanism which corresponds to the phase-difference motor are in mesh with each other, backlash occurs between the output gear and the input gear. When such backlash occurs, the rotational control of the pair of aperture controlling rotary plates cannot be correctly carried out.

Furthermore, the above described problem also occurs in the same manner when the rotational force of the phase difference motor is reduced in speed or increased in speed in the case where a gear mechanism having a plurality of gears is provided between the phase difference motor and the above-mentioned output gear.

SUMMARY OF THE INVENTION

The present invention provides a light source apparatus for an electronic endoscope which performs a rotational control of a pair of aperture controlling rotary plates by utilizing a planetary gear mechanism, wherein by reducing the amount of backlash between an input gear of the planetary gear mechanism and the output gear of a phase difference motor and the amount of backlash between the phase difference motor and the output gear thereof, more than that of the prior art, the accuracy of the rotational control of the pair of aperture controlling rotary plates is increased.

According to an aspect of the present invention, a light source apparatus for an electronic endoscope is provided, including a light source; a rotary shutter, having a rotation axis, which includes a pair of coaxial aperture controlling rotary plates, wherein an amount of light emitted from the light source toward a light guide is controlled by varying a relative rotation angle of the pair of aperture controlling rotary plates; a first planetary gear mechanism including a first internal tooth gear, which is a fixed gear and is coaxial with the rotation axis of the rotary shutter, a first sun gear which is rotated together with one of the pair of aperture controlling rotary plates via a motor and is coaxial with an axis of the first internal tooth gear, and at least one first planet gear which is simultaneously engaged with the first internal tooth gear and the first sun gear; a second planetary gear mechanism including a second internal tooth gear identical to the first internal tooth gear and coaxial with the rotation axis of the rotary shutter, a second sun gear which rotates together with the other of the pair of aperture controlling rotary plates and is identical to the first sun gear and coaxial with an axis of the second internal tooth gear, and at least one second planet gear, identical to the first planet gear, which is simultaneously engaged with the second internal tooth gear and the second sun gear; and a carrier device which is rotatable about an axis coincident with the rotation axis of the rotary shutter, wherein the carrier device holds the first and second planet gears in a same phase position with respect to the first and second internal tooth gears, and supports the first and second planet gears to allow the first and second planet gears to rotate relative to each other. An endless timing belt, formed from a resilient material, is installed on an output gear which is fixed to a drive shaft of a phase-difference motor which is provided separate from the motor and an input tooth portion formed on an outer peripheral surface of the second internal tooth gear. The timing belt includes a meshing portion formed on an inner peripheral surface thereof, the meshing portion being engaged with the input tooth portion of the second internal tooth gear and the output gear.

In an embodiment, a light source apparatus for an electronic endoscope is provided, including a light source; a rotary shutter, having a rotation axis, which includes a pair of coaxial aperture controlling rotary plates, wherein an amount of light emitted from the light source toward a light guide is controlled by varying a relative rotation angle of the pair of aperture controlling rotary plates; a first planetary gear mechanism including a first internal tooth gear, which is coaxial with the rotation axis of the rotary shutter, a first sun gear which is driven to rotate together with one of the pair of aperture controlling rotary plates via a motor and is coaxial with an axis of the first internal tooth gear, and at least one first planet gear which is simultaneously engaged with the first internal tooth gear and the first sun gear; a second planetary gear mechanism including a second internal tooth gear, which is a fixed gear, identical to the first internal tooth gear and coaxial with the rotation axis of the rotary shutter, a second sun gear which rotates together with the other of the pair of aperture controlling rotary plates and is identical to the first sun gear and coaxial with an axis of the second internal tooth gear, and at least one second planet gear, identical to the first planet gear, which is simultaneously engaged with the second internal tooth gear and the second sun gear; and a carrier device which is rotatable about an axis coincident with the rotation axis of the rotary shutter, wherein the carrier device holds the first and second planet gears in a same phase position with respect to the first and second internal tooth gears, and supports the first and second planet gears to allow the first and second planet gears to rotate relative to each other. An endless timing belt, formed from a resilient material, is installed on an output gear which is fixed to a drive shaft of a phase-difference motor which is provided separate from the motor and an input tooth portion formed on an outer peripheral surface of the first internal tooth gear, and the timing belt includes a meshing portion formed on an inner peripheral surface thereof, the meshing portion being engaged with the input tooth portion of the second internal tooth gear and the output gear.

It is desirable for the first internal tooth gear to be rotatably supported by a gear bearing.

In an embodiment, an electronic endoscope having the light source apparatus is provided, including an operating portion; and an insertion portion extending from the operating portion and inserted into an object to be viewed. The light guide is inserted in the operating portion and the insertion portion so that a distal end of the light guide extends to a distal end of the insertion portion, and the light source emits illuminating light to the light guide.

According to the present invention, the amount of backlash between the input gear of the planetary gear mechanism and the output gear of the phase difference motor is reduced more than that of the prior art, and furthermore, since no backlash exists between the drive shaft of the phase difference motor and the output gear thereof, it is possible to rotationally control the pair of aperture controlling rotary plates more accurately than those of the prior art.

The present disclosure relates to subject matter contained in Japanese Patent Application No. 2005-176098 (filed on Jun. 16, 2005) which is expressly incorporated herein in its entirety.

BRIEF DESCRIPTION OF THE DRAWINGS

The present invention will be discussed below in detail with reference to the accompanying drawings, in which:

FIG. 3C is a front elevation view of a rotary shutter consisting of the first aperture controlling rotary plate shown in FIG. 3A and the second aperture controlling rotary plate shown in FIG. 3B;

DESCRIPTION OF THE PREFERRED EMBODIMENTS

A first embodiment of a light source apparatus according to the present invention will be discussed below with reference to FIGS. 1 through 5.

Figure 1:
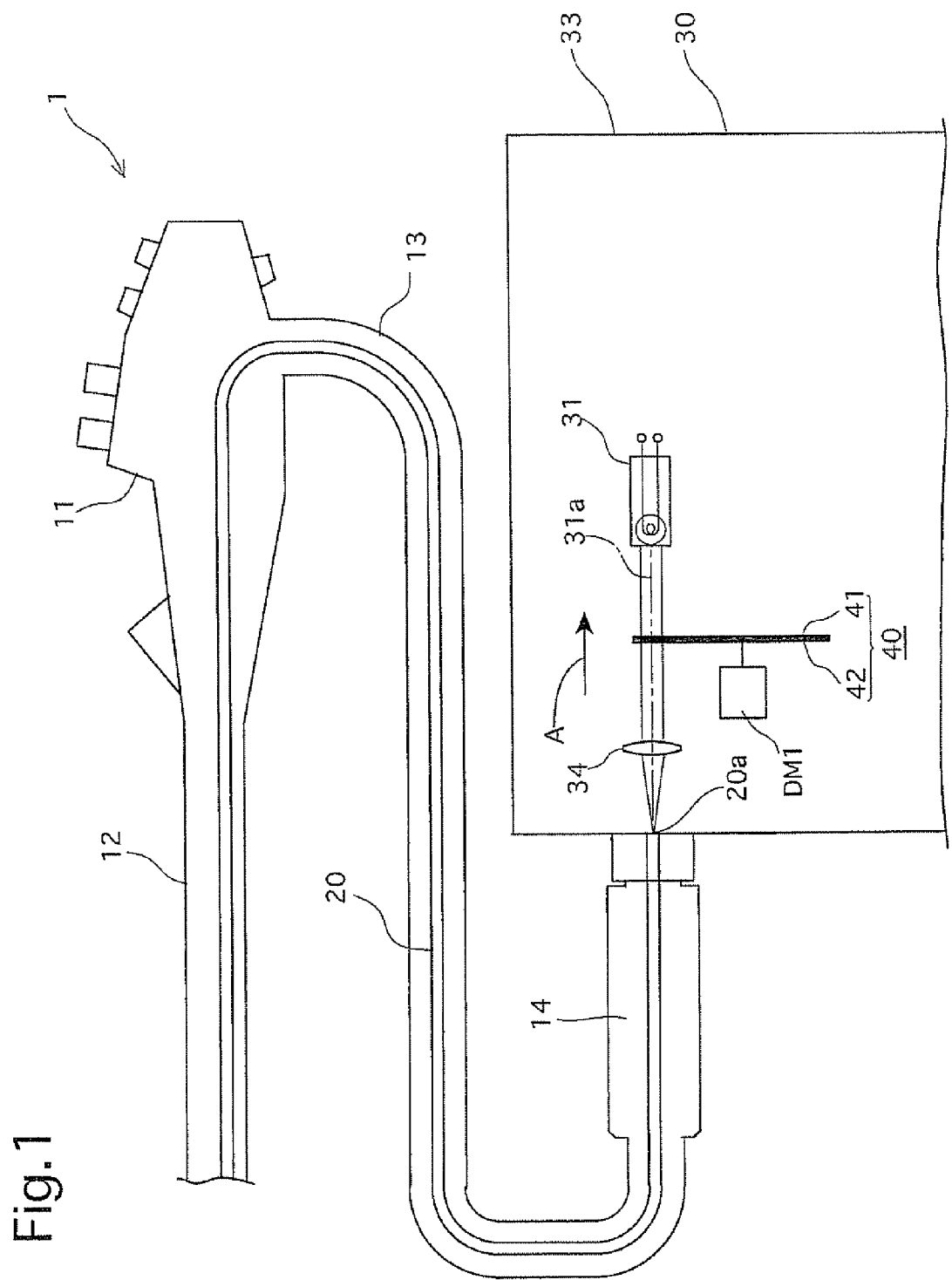
FIG. 1 is a schematic view of an electronic endoscope system including an electronic endoscope and a first embodiment of a light source apparatus according to the present invention, showing an internal structure of the light source apparatus.

As shown in FIG. 1, an electronic endoscope 1 of the present invention includes an operating portion 11 which is held by an operator, a flexible and elongated insertion portion 12 extending from the operating portion 11, a universal tube 13 extending from the operating portion 11, and a connector portion 14 connected to the end of the universal tube 13. A light guide (light guide fiber bundle) 20 is provided in the operating portion 11, the insertion portion 12, the universal tube 13, and the connector portion 14. The distal end of the light guide 20 is connected to an illumination optical system (not shown) provided on the distal end of the insertion portion 12 to emit illuminating light out of the endoscope 1.

The connector portion 14 of the electronic endoscope 1 is connected to a light source apparatus (video processor) 30. The light source apparatus 30 is provided in a casing 33 thereof with a lamp (light source) 31. Light (illuminating light) emitted from the lamp 31 is incident upon the light guide 20 at the incident end surface 20a thereof. The light transmitted through the light guide 20 is emitted to the outside of the electronic endoscope 1 from the illumination optical system at the distal end of the insertion portion 12. Illumination light (reflected light) which is reflected by a viewed object is incident upon the insertion portion 12 through an objective optical system 15 provided at the distal end of the insertion portion 12, and is accumulated as electric charges in a CCD (solid image pickup device) 16 (see FIG. 2) provided inside the distal end of the insertion portion 12. All of the image pixel data of the CCD 16 is sent to an image processing circuit (image processor) 18 and is processed in the image processing circuit 18, and an image corresponding to the image pixel data is displayed on a display 19 (see FIG. 2).

The light source apparatus 30 includes, in addition to the lamp 31, a rotary shutter 40 which functions as a light controller for controlling or intercepting illuminating light emitted from the lamp 31 (having an optical axis 31a), a condenser lens 34 which condenses the light emitted from the lamp 31 and guides the light to the incident end surface 20a of the light guide 20, and a drive mechanism DM1 for driving the rotary shutter 40.

Figure 3A:
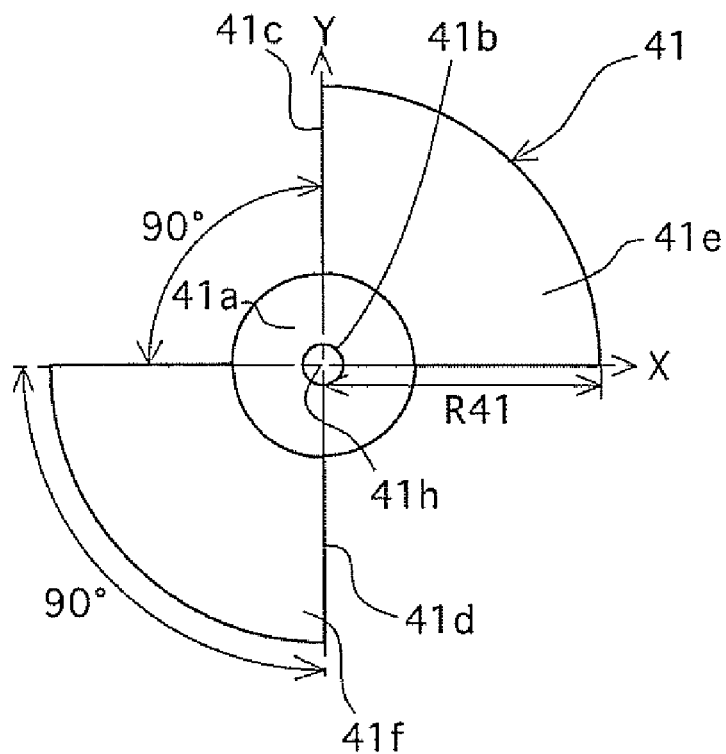
FIG. 3A is a front elevational view of a first aperture controlling rotary plate.
Figure 3B:
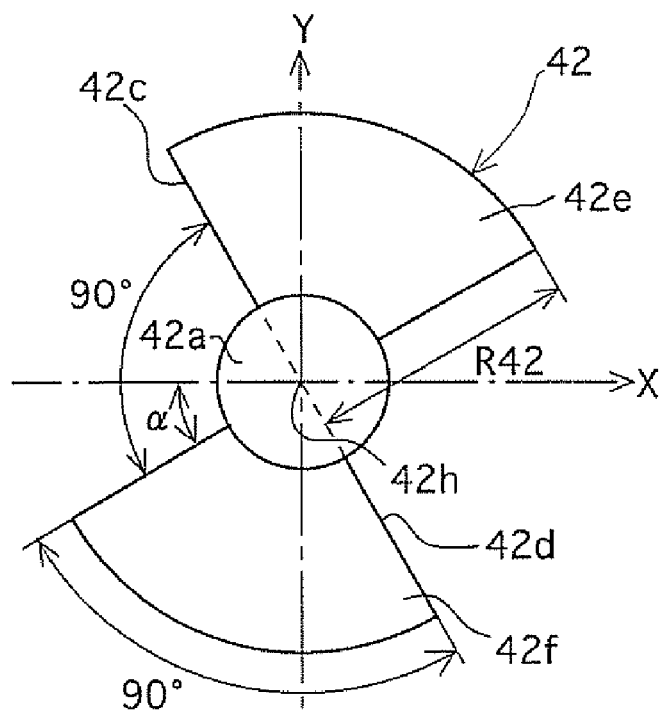
FIG. 3B is a front elevational view of a second aperture controlling rotary plate.

As shown in FIGS. 3A through 3C, the rotary shutter 40 is provided with a first aperture controlling rotary plate 41 and a second aperture controlling rotary plate 42 which have substantially the same outer shape. The first aperture controlling plate 41 that is shown in FIG. 3A is an aluminum flat plate provided perpendicular to the optical axis 31a, and includes a circular center portion 41a and a pair of light intercepting portions 41e and 41f which are directly joined to the central portion 41a. The circular central portion 41a is provided at the center thereof with a circular center hole 41b. The pair of light intercepting portions 41e and 41f are arranged symmetrically with respect to the rotational center 41h of the central portion 41a, and are each substantially in the form of a sector having a central angle of 90 degrees which is centered on the rotational center 41h. Opening portions 41c and 41d, each having an angle of 90 degrees with respect to the rotational center 41h are formed between the light intercepting portions 41e and 41f. As shown in FIG. 3A, the linear distance (radius of the first aperture controlling rotary plate 41) between the rotational center 41h and the outer edge of either of the light intercepting portions 41e and 41f is R41.

The second aperture controlling plate 42 shown in FIG. 3B is aluminum flat plate provided perpendicular to the optical axis 31a, and includes a disc portion 42a at the center of the second aperture controlling plate 42 and a pair of light intercepting portions 42e and 42f. The light intercepting portions 42e and 42f are arranged symmetrically with respect to the rotational center 42h of the central disc portion 42a, and are each substantially in the form of a sector having a central angle of 90 degrees which is centered on the rotational center 42h. Opening portions 42c and 42d, each having an angle of 90 degrees with respect to the rotational center 42h, are formed between the light intercepting portions 42e and 42f. As shown in FIG. 3B, the linear distance (radius of the second aperture controlling rotary plate 42) between the rotational center 42h and the outer periphery of either of the light intercepting portions 42e and 42f is R42 (<R41).

The radii R41 and R42 are determined to be equal to or greater than the diameter of the light bundle emitted from the lamp 31 and made incident upon the rotary shutter 40. Provided that this requirement is met, R41 can be equal to or smaller than R42 (R41=R42 or R41<R42). Although the opening portions and the light intercepting portions have a center angle of 90 degrees with respect to the respective rotational centers 41h and 42h in the first and second aperture controlling rotary plates 41 and 42 in the illustrated embodiment, the center angle may be other than 90 degrees and the first and second aperture controlling rotary plates 41 and 42 may be different in shape.

Figure 4:
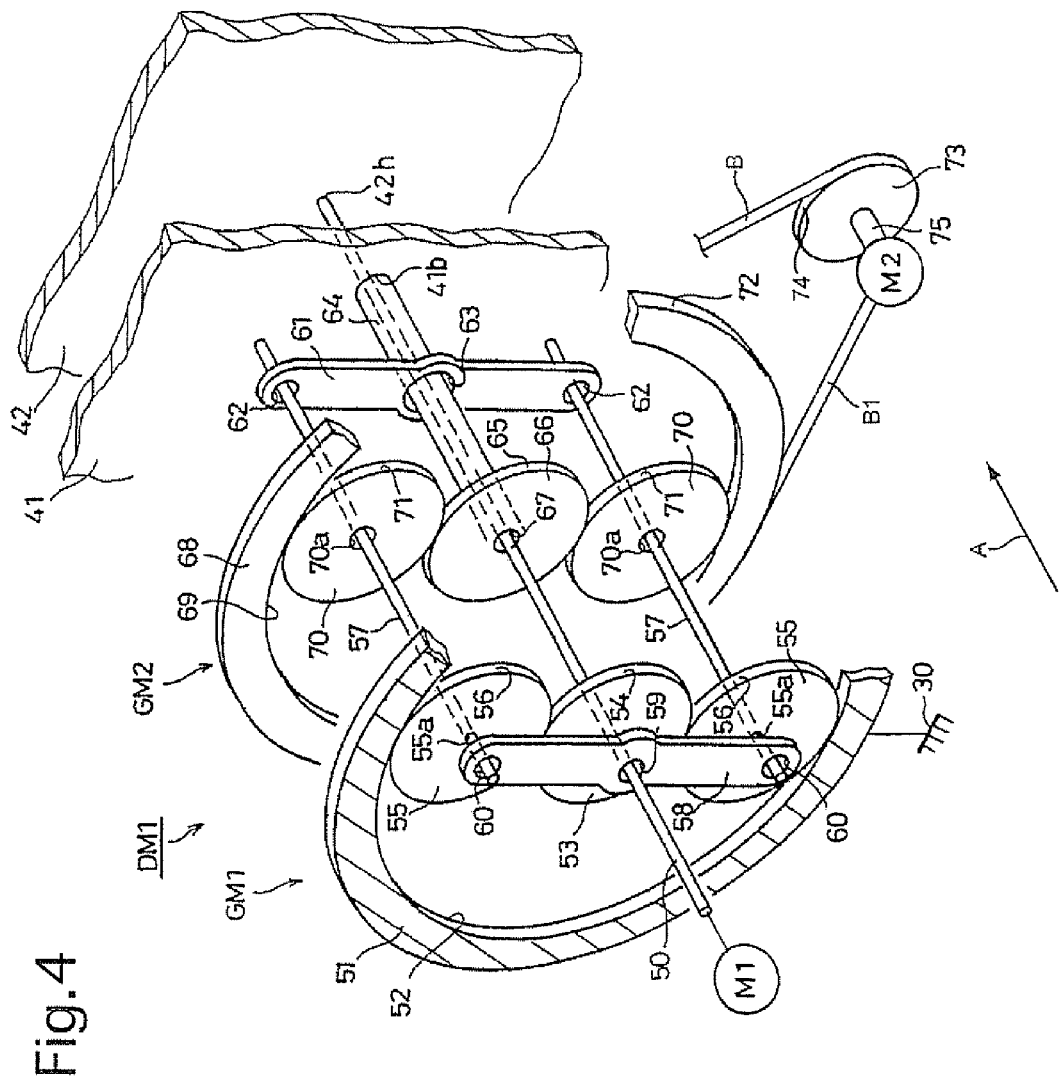
FIG. 4 is an exploded perspective schematic diagram of a drive mechanism for driving the rotary shutter shown in FIG. 3C.

As shown in FIG. 3C, if the rotational centers 41h and 42h of the first and second aperture controlling rotary plates 41 and 42 are arranged to be coincident with each other (aligned each other), if the first aperture controlling rotary plate 41 is arranged so that the light intercepting portions 41e and 41f are located within the first quadrant and the third quadrant in X-Y coordinates (abscissa X and ordinate Y), respectively, and further if the second aperture controlling rotary plate 42 is arranged so that the light intercepting portions 42e and 42f are deviated by an angle α in the counterclockwise direction (as viewed in a direction from the condenser lens 34 side toward the lamp 31; see arrow "A" in FIGS. 1 and 4; likewise with the second embodiment (see arrow "A" in FIG. 6)) with respect to the light intercepting portions 41e and 41f, respectively, the opening portions 41c and 41d are partly covered by the light intercepting portions 42e and 42f, respectively. The opening portions 40c and 40d of the rotary shutter 40 thus obtained are substantially in the form of sectors which are arranged symmetrically with respect to the rotational centers 41h and 42h and which have a center angle (opening angle) θ equal to 90−α degrees. The opening angle θ can be varied between a range of 0 (smallest angle) to 90 degrees (largest angle) by relatively rotating the first and second aperture controlling rotary plates 41 and 42.

The drive mechanism DM1 for rotating the first aperture controlling rotary plate 41 and the second aperture controlling rotary plate 42 will be explained below with reference to FIGS. 4 and 5.

The drive mechanism DM1 is provided with a drive shaft (rotating shaft) 50 which extends perpendicularly to the first and second aperture controlling rotary plates 41 and 42 (i.e., parallel with the optical axis 31a) and which relatively rotatably extends through the center hole 41b that is formed in the first aperture controlling rotary plate 41. An end of the drive shaft 50 is fixed to the rotational center 42h of the second aperture controlling rotary plate 42. The rotational centers 41h and 42h are coaxial with the drive shaft 50 and with an extended line from the drive shaft 50. A drive shaft of a chopper motor (pulse motor) M1, secured to the casing 33 of the light source apparatus 30, is fixed to the other end of the drive shaft 50 to be coaxial therewith (i.e., "coaxial" when viewed from the direction of the arrow "A" shown in FIGS. 4 and 6) so that rotation of the chopper motor M1 causes the drive shaft 50 to rotate about the axis thereof. The drive mechanism DM1 is provided around the drive shaft 50 with an internal tooth gear (first internal tooth gear) 51 in the form of a ring coaxial with the drive shaft 50. The internal tooth gear 51 is secured to the casing 33 of the light source apparatus 30 (the internal tooth gear 51 is hatched in FIG. 4 to indicate that the internal tooth gear is a stationary member). The internal tooth gear 51 is provided, on its entire inner peripheral surface, with sixty internal teeth 52 at equal pitches. The detailed shape of the internal teeth 52 (and all the other gears which will be discussed later) is not shown for the purpose of simplicity. The drive mechanism DM1 is provided with a first circular sun gear 53 which is smaller in diameter than the internal tooth gear 51 and which lies in the same plane as the internal tooth gear 51. The drive shaft 50 extends through the center of the first sun gear 53r and the first sun gear 53 is coaxially fitted on the drive shaft 50 and fixed thereto. The first sun gear 53 is provided on the entire outer edge thereof with twenty four external teeth 54 at equal pitches. The drive mechanism DM1 is provided between the internal tooth gear 51 and the first sun gear 53 with two first planet gears 55. The first planet gears 55 are each provided with eighteen external teeth 56 at equal pitches. The first planet gears 55 are identical in diameter to the first sun gear 53 and are arranged symmetrically with respect to the first sun gear 53. The external teeth 56 of each first planet gear 55 are in mesh with the internal teeth 52 of the internal tooth gear 51 and the external teeth 54 of the first sun gear 53. Each first planet gear 55 is provided with a circular mount hole 55a at the central portion thereof. The drive mechanism DM1 is provided on opposite sides of the drive shaft 50 with two driven shafts 57 extending parallel to the drive shaft 50, respectively, and end portions of the two driven shafts 57 which are located adjacent to the chopper motor M1 are fitted in the mount holes 55a of the first planet gears 55 to be fixed thereto, respectively. The drive mechanism DM1 is provided with a first carrier (carrier device) 58 in between the chopper motor M1, and the internal tooth gear 51, the first sun gear 53 and the first planet gears 55. The first carrier 58 extends in a radial direction of the internal tooth gear 51. The first carrier 58 is provided on a center portion (rotation center) thereof with a round center hole 59 through which the drive shaft 50 extends to be rotatable relative to the round center hole 59. The first carrier 58 is provided on its opposite ends with engagement holes 60 in which the ends of the driven shafts 57 adjacent to the chopper motor M1 are inserted to be rotatable relative to the engagement holes 60, respectively.

The internal tooth gear 51, the first sun gear 53 and the first planet gears 55 constitute a first planetary gear mechanism GM1.

The drive mechanism DM1 is provided with a second carrier (carrier plate) 61 adjacent to the first aperture controlling rotary plate 41. The second carrier 61 is provided on its opposite ends with engagement holes 62 in which the ends of the driven shafts 57 adjacent to the first aperture controlling rotary plate 41 are inserted to be rotatable relative to the engagement holes 62, respectively. The second carrier 61 is provided on a center portion (rotation center) thereof with a circular hole 63. A rotary cylinder 64 which is relatively rotatable with respect to the drive shaft 50 is provided coaxially to the drive shaft 50 and is provided around the periphery of the end of the drive shaft 50 at the first aperture controlling plate 41 side. The rotary cylinder 64 extends through the circular hole 63 so as to be relatively rotatable with respect thereto. The rotary cylinder 64 is fixed, on an end surface thereof on the chopper motor M1 side, to the center of a second circular sun gear 66 which is arranged coaxially with the first sun gear 53 and has the same diameter as the first sun gear 53. The second sun gear 66 is provided on an outer edge thereof with twenty four external teeth 65 having the same specifications as the external teeth 54 of the first sun gear 53. Furthermore, the second sun gear 66 is provided at a center thereof with a center hole 67 which is formed as a through-hole, through which the drive shaft 50 extends so as to be relatively rotatable thereto. The end portion of the rotary cylinder 64, on the second aperture controlling rotary plate 42 side, is fitted in the center hole 41b of the first aperture controlling plate 41 to be fixed thereto so that the internal space of the rotary cylinder 64 is communicably connected with the center hole 41b. An internal/external tooth gear (second internal tooth gear) 68 coaxial with the second sun gear 66 is provided around the second sun gear 66 and is rotatable about the drive shaft 50. The second internal tooth gear 68 lies in the same plane as the second sun gear 66. The second internal tooth gear 68 is provided on its inner peripheral surface with internal teeth 69 having the same specifications as the internal teeth 52 of the internal tooth gear 51. Furthermore, the drive mechanism DM1 is provided between the internal/external tooth gear 68 and the second sun gear 66 with two second planet gears 70. The planet gears 70 are each provided with external teeth 71 having the same specifications as the external teeth 56 of each first planet gear 55. The planet gears 70 are identical in diameter to the first planet gears 55 and are arranged symmetrically with respect to the second sun gear 66. The driven shafts 57 are rotatably inserted into center holes 70a of the second internal tooth gears 70. The external teeth 71 of each second planet gear 70 are in mesh with both the internal teeth 69 of the internal/external tooth gear 68 and the external teeth 65 of the second sun gear 66. The internal/external tooth gear 68 is provided on its entire outer peripheral surface with external teeth (input tooth portion) 72 having the same pitch.

A phase difference motor (pulse motor) M2, fixed to the casing 33 of the light source apparatus 30, is provided in the vicinity of the internal/external tooth gear 68. A center portion of a drive gear (output gear) 73, which is provided on a common plane with that of the internal/external tooth gear 68, is directly fixed to a drive shaft (output shaft) 75 which is provided so as to extend from the phase difference motor M2 and extend in a direction parallel to the drive shaft 50. The drive gear 73 is provided on its entire outer peripheral surface with external teeth 74 having an equal pitch. Furthermore, a looped endless timing belt B formed from a resilient material such as rubber, etc., is installed in a tensioned state on the external teeth 72 of the internal/external tooth gear 68 and on the external teeth 74 of the drive gear 73. The endless timing belt B has a plurality of inner peripheral teeth (meshing portion) B1 formed on the inner peripheral surface thereof at an equal pitch (the same pitch as that of the external teeth 72 and the external teeth 74) and are in mesh with the external teeth 72 and the external teeth 74. Accordingly, the drive gear 73 (external teeth 74) and the internal/external tooth gear 68 (external 72) are interconnected via the endless timing belt B.

The second sun gear 66, the internal/external tooth gear 68 and the second planet gears 70 constitute a second planetary gear mechanism GM2.

Figure 2:
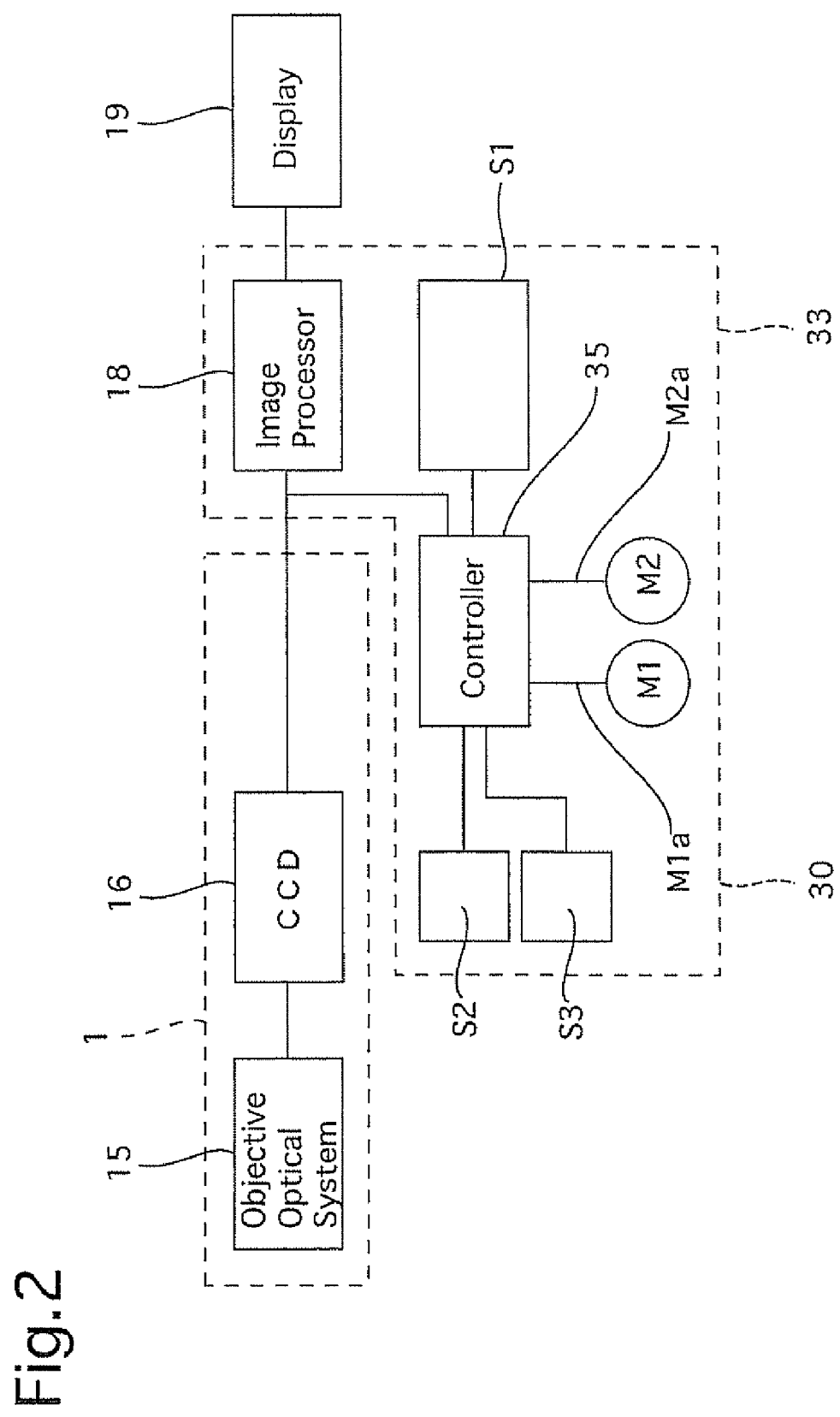
FIG. 2 is a block diagram of the electronic endoscope system shown in FIG. 1.

As shown in FIG. 2, harnesses (electric wires) M1a and M2a extend from the body of the chopper motor M1 and the body of the phase difference motor M2 and are electrically connected to a controller (control device) 35 which includes a CPU (central processing unit) incorporated in the light source apparatus 30. The controller 35 controls operations of the chopper motor M1 and the phase difference motor M2 and calculates the brightness of the object based on a brightness signal supplied from the CCD 16. The light source apparatus 30 is provided therein with an automatic light control switch S1, a chopper motor control button S2 and a phase difference motor control button S3 all of which are electrically connected to the controller 35.

Operations of the drive mechanism DM1 and the rotary shutter 40 will be discussed below with reference mainly to FIGS. 4 and 5.

Although drive forces of the chopper motor M1 and the phase difference motor M2 are transferred to elements of the drive mechanism DM1, only the drive force of the chopper motor M1 will be considered in the first place in the following description for the purpose of making the operation of the drive mechanism DM1 easy to understand.

When the chopper motor M1 is rotated in the clockwise direction upon drive pulses being sent to the chopper motor M1 by the controller 35, the drive gear 50 and the first sun gear 53 rotate in the clockwise direction at a rotation speed SP1. Thereupon, each of the two first planet gears 55 rotates on the associated driven shaft 57 in the counterclockwise direction while revolving around the drive shaft 50 in the clockwise direction. At the same time, the second carrier 61 which is synchronized with the first carrier 58 through the driven shafts 57 (i.e., the second carrier 61 is always located at the same phase position as the first carrier 58 with respect to the internal tooth gear 51 and the internal/external tooth gear 68)

rotates in the clockwise direction, so that each of the two second planet gears 70 rotates on the associated driven shaft 57 in the counterclockwise direction while revolving about the drive shaft 50 in the clockwise direction. At this time, the rotation speed and the revolution speed of each second planet gear 70 are the same as those of each first planet gear 55. Therefore, the second sun gear 66 rotates in the clockwise direction at the rotation speed SP1.

As can be understood from the foregoing description, the second sun gear 66 obtains the same rotation speed SP1 as the first sun gear 53 from the chopper motor M1. However, in the case where the drive force of the phase difference motor M2 is also transferred to the second sun gear 66, the second sun gear 66 rotates at a rotation speed different from the rotation speed SP1.

Namely, when the controller 35 sends a pulse signal to the phase difference motor M2 so that the phase difference motor M2 rotates in a rotation direction the same as the rotation direction of the chopper motor M1, the rotational force of the phase difference motor M2 is transferred to the external teeth 72 via the inner peripheral teeth B1 of the endless timing belt B and the external teeth 74 of the drive gear 73 to rotate the internal/external tooth gear 68 in the clockwise direction. Accordingly, the rotational force of the internal/external tooth gear 68 is transferred to the second planet gears 70, so that the rotation speed of each of the two second planet gears 70 on the associated driven shaft 57 in the counterclockwise direction and the clockwise revolving speed of the second planet gears 70 becomes greater than when each second planet gear 70 is driven only by the drive force of the chopper motor M1. Therefore, the second sun gear 66 in mesh with the second planet gears 70 rotates in the clockwise direction at a rotation speed SP2 higher than the rotation speed SP1 of the first sun gear 53.

When the phase difference motor M2 is rotated in the opposite direction as the chopper motor M1, the internal/external tooth gear 68 rotates in the counterclockwise direction, so that the rotation speed of each of the two second planet gears 70 on the associated driven shaft 57 in the counterclockwise direction and the clockwise revolving speed of the second planet gears 70 becomes lower than that when each second planet gear 70 is driven only by the drive force of the chopper motor M1. Consequently, the second sun gear 66 rotates in the clockwise direction at a rotation speed SP3 lower than the rotation speed SP1.

When there is a difference between the rotation speed SP2 (SP3) of the second sun gear 66 and the rotation speed SP1 of the first sun gear 53, a difference in rotation speed occurs between the first aperture controlling rotary plate 41 and the second aperture controlling rotary plate 42, and accordingly, the opening angle θ of each opening portion 40c and 40d gradually varies within the range of 0 to 90 degrees.

Automatic and manual light control using the drive mechanism DM1 can be carried out in the light source apparatus 30. When the automatic light control and the manual light control are carried out, the insertion portion 12 of the electronic endoscope 1 is inserted into the patient's body (viewing object) and the viewing site therein is illuminated with the illuminating light emitted from the lamp 31 via the rotary shutter 40, the condenser lens 34 and the light guide 20, wherein the controller 35 constantly detects the brightness of the viewing site based on the brightness signal supplied from the CCD 16.

Upon the automatic light control switch S1 being turned ON, the controller 35 which receives a command from the automatic light control switch S1 automatically sends a pulse signal to the chopper motor M1 and the phase difference motor M2 and automatically controls the rotation direction and the rotation speed of the chopper motor M1 and the phase difference motor M2, in accordance with the brightness signal from the CCD 16 to vary the opening angle θ of each opening portion 40c and 40d in the range of 0 to 90 degrees to thereby vary the quantity of illuminating light transmitted through the rotary shutter 40 so that the brightness of the viewing site is always at a desired value.

In the manual light control, in a state where the automatic light control switch S1 is OFF, the chopper motor control button S2 and the phase difference motor control button S3 are manually operated, and pulse signals are sent from the controller 35 to the chopper motor M1 and the phase difference motor M2.

In this case, firstly the chopper motor M1 and the phase difference motor M2 are rotated by manually operating the chopper motor control button S2 and the phase difference control button S3. Thereafter, upon the opening angle θ of each opening portion 40c and 40d becoming a desired value, the phase difference motor M2 is stopped by an operation of the phase difference motor control button S3 so that the opening angle θ of each opening portion 40c and 40d is maintained at the desired value. When the transmission of the drive force from the phase difference motor M2 to the second sun gear 66 is interrupted in this manner so that the second sun gear 66 is rotated only by the chopper motor M1, the first aperture controlling rotary plate 41 and the second aperture controlling rotary plate 42 rotate in the same direction at the same speed while maintaining the desired opening angle θ. Additionally, since the rotation speed of the chopper motor M1 and the phase difference motor M2 can be controlled by operating the chopper motor control button S2 and the phase difference motor control button S3, respectively, an operator (user) can manually and freely control the quantity of illuminating light to be transmitted to the light guide 20.

According to the above described embodiment of the light source apparatus, the inner peripheral teeth B1 of the endless timing belt B, which is formed by a resilient material, meshes with the external teeth 74 of the drive gear 73 and the external teeth 72 of the internal/external tooth gear 68, and since the rotational force of the drive gear 73 is transmitted to the internal/external tooth gear 68 via the endless timing belt B, backlash between the drive gear 73 (external teeth 74) and the internal/external tooth gear 68 (external teeth 72) is negligible. Accordingly, the rotational control of the first aperture controlling rotary plate 41 and the second aperture controlling rotary plate 42 can be carried out more precisely than in the prior art.

Furthermore, if a pulse motor having a small step angle (e.g., a step angle of 1.8°) is used as the phase difference motor M2, the rotational force of the phase difference motor M2 can be transmitted to the internal/external tooth gear 68 (external teeth 72) at a low rotational speed even without a gear mechanism (reduction mechanism) provided between the phase difference motor M2 and the drive gear 73. In the case where a gear mechanism (reduction mechanism) is used, the precision of the rotational control of the first aperture controlling rotary plate 41 and the second aperture controlling rotary plate 42 is reduced due to backlash occurring between adjacent (meshing) gears and backlash occurring between the output gear of the gear mechanism and the drive gear 73. However, if a pulse motor having a small step angle is used, since it is possible to rotate the drive gear 73 at a low speed thereby while being able to directly attach the drive shaft 75 of the pulse motor (phase difference motor M2) to the drive gear 73, there is the advantage of backlash not existing between the phase difference motor M2 and the drive gear 73.

Furthermore, the main bodies of the chopper motor M1 and the phase difference motor M2 of the drive mechanism DM1 do not rotate, and hence, the harnesses (electric wires) M1a and M2a thereof are not twisted or bent in accordance with rotations of the chopper motor M1 and the phase difference motor M2. Therefore, it is not necessary to provide any specific device for preventing interference of the harnesses M1a and M2a.

Figure 6:
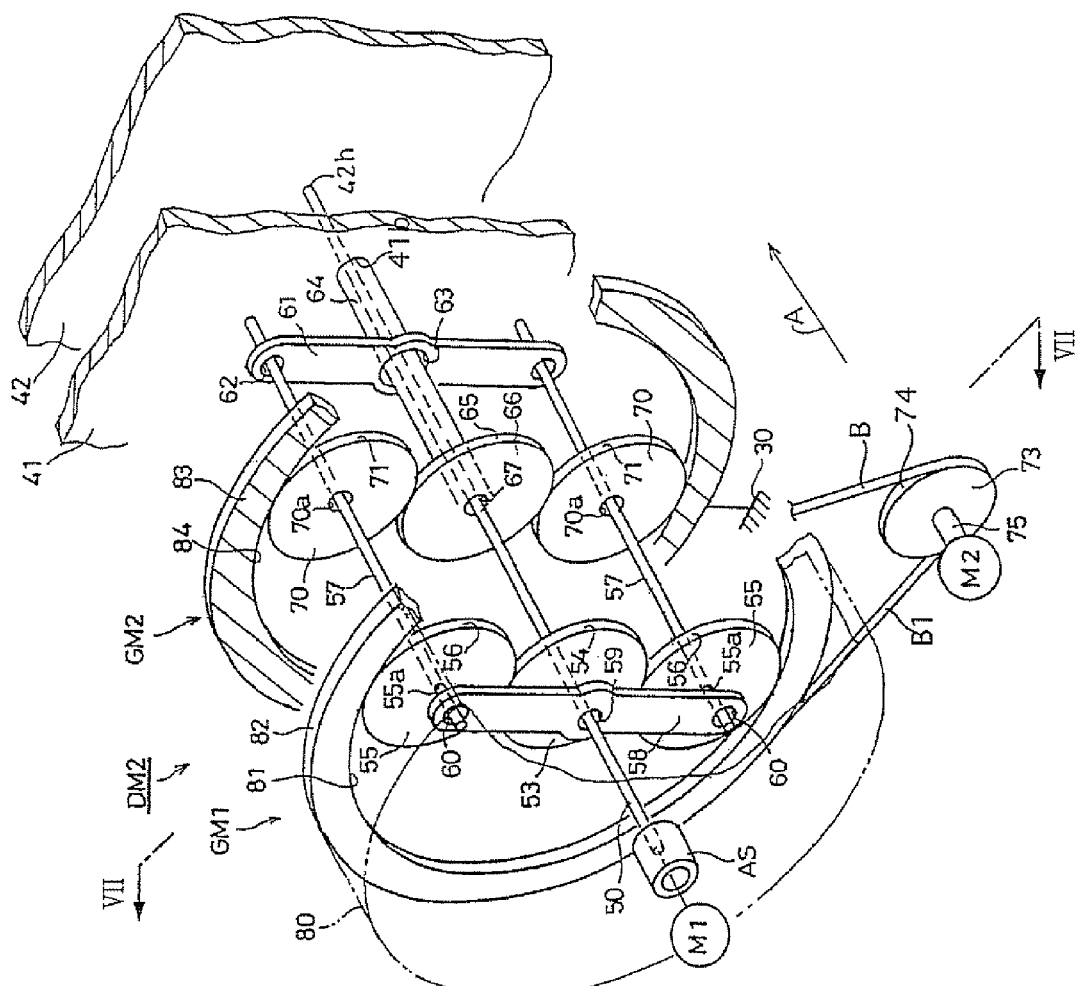
FIG. 6 is a schematic view similar to that of FIG. 4, showing a drive mechanism for driving the rotary shutter shown in FIG. 3C in a second embodiment of the light source apparatus according to the present invention.
Figure 7:
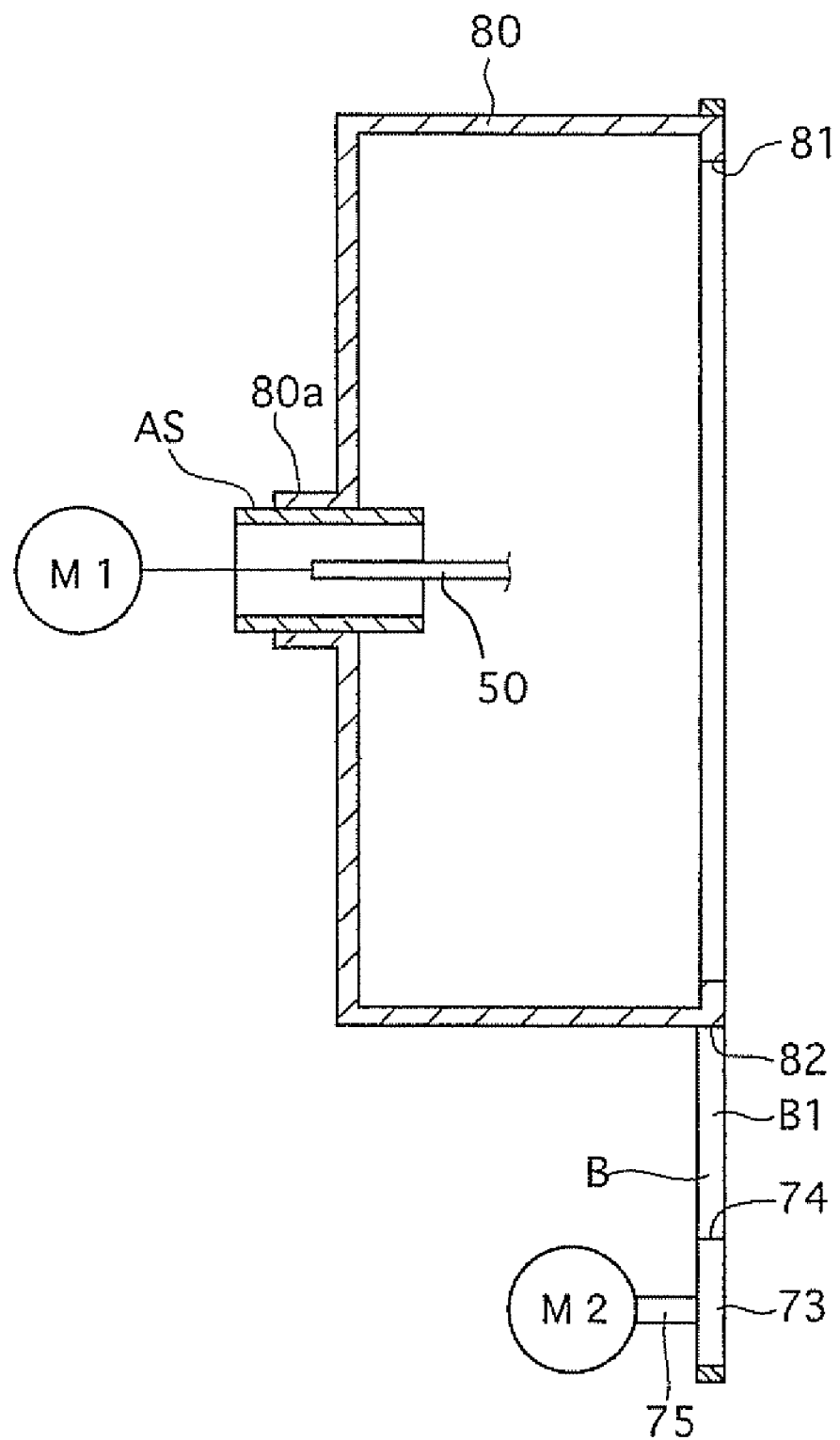
FIG. 7 is a cross sectional view taken along VII-VII line shown in FIG. 6.
Figure 8:
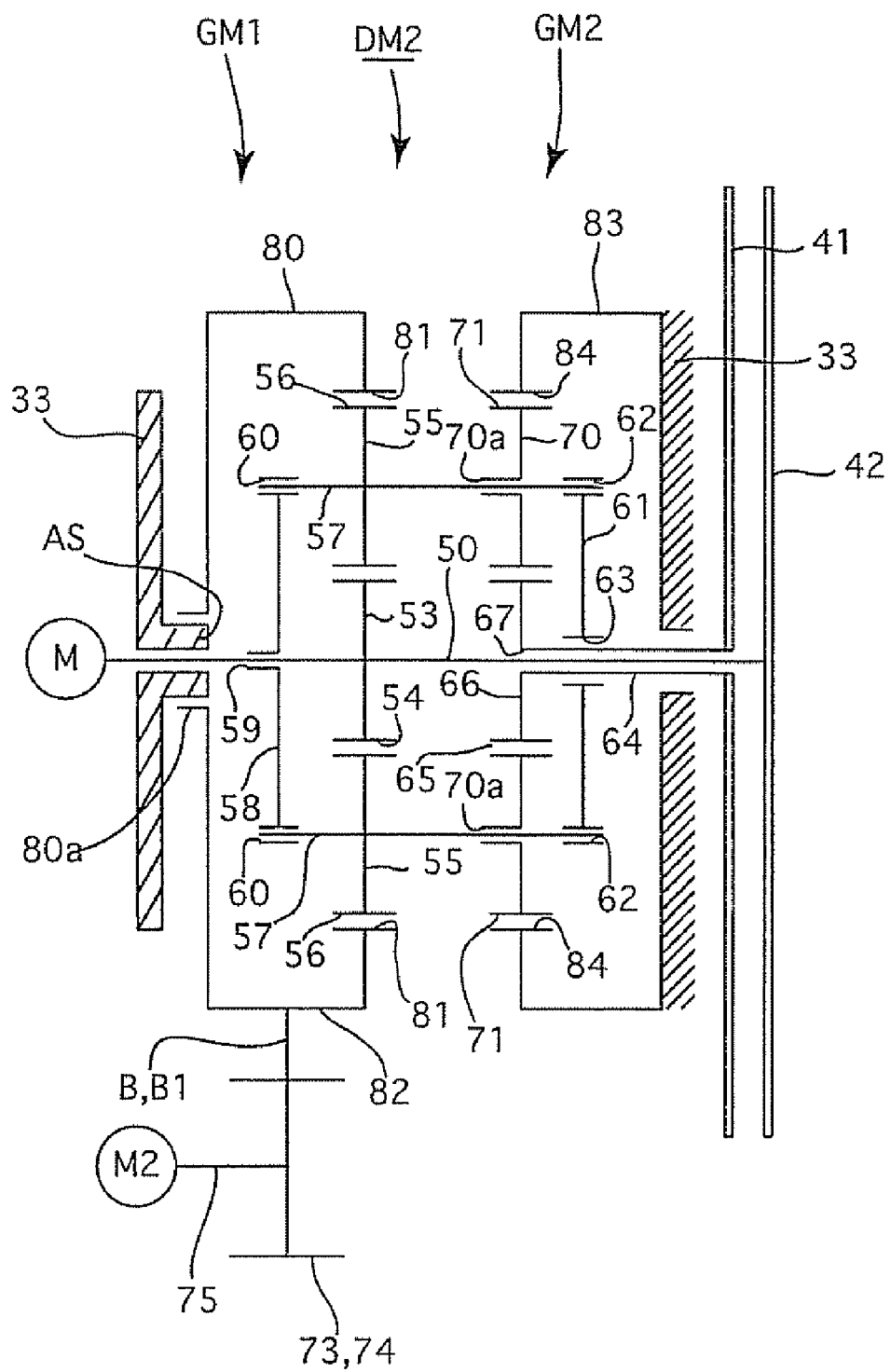
FIG. 8 shows the drive mechanism shown in FIG. 6 and elements on the periphery thereof.

A second embodiment of the light source apparatus according to the present invention will be hereinafter discussed with reference mainly to FIGS. 6 through 8.

The second embodiment of the light source apparatus is different from the first embodiment of the light source apparatus only in the drive mechanism DM2, and accordingly, the elements corresponding to those in the first embodiment are designated by like reference numerals and no detailed explanation thereof will be given below.

A stationary bearing (gear bearing) AS secured to the casing 33 of the light source apparatus 30 is provided around the drive shaft 50 and the drive shaft of the chopper motor M1. The stationary bearing AS is in the form of a cylinder having open ends and is positioned to be coaxial with the drive shaft 50 and the drive shaft of the chopper motor M1. The second embodiment of the light source apparatus is provided, instead of the internal tooth gear 51 and the internal/external tooth gear 68 in the first embodiment of the light source apparatus, with an internal/external tooth gear (first internal tooth gear) 80 and an internal tooth gear (second internal tooth gear) 83, respectively. The internal/external tooth gear 80 is substantially cylindrical and is provided, on its end wall on the chopper motor M1 side, with a central cylindrical fitting portion 80a (see FIG. 7) coaxial with the drive shaft 50 and integral with the internal/external tooth gear 80. The stationary bearing AS is fitted in the cylindrical fitting portion 80a so as to relatively rotate about the drive shaft 50. Note that the inner diameter of the cylindrical fitting portion 80a is the same as the outer diameter of the stationary bearing AS. The internal/external tooth gear 80 is identical in diameter to the internal tooth gear 51 shown in FIGS. 4 and 5 of the first embodiment. The internal/external tooth gear 80 is provided, on its end surface on the first aperture controlling rotary plate 41 side, with a circular opening coaxial with the drive shaft 50. Internal teeth 81 identical to the internal teeth 52 of the internal tooth gear 51 are formed along the entire inner peripheral surface of the circular opening of the internal/external tooth gear 80. External teeth 82 identical to the external teeth 72 of the second internal tooth gear 68 of the first embodiment (shown in FIGS. 4 and 5) are formed entirely on an annular end portion of the outer peripheral surface of the internal/external tooth gear 80 on the first aperture controlling rotary plate 41 side.

A phase difference motor M2, which is a pulse motor and the same as that of the first embodiment, is provided in the vicinity of the internal/external tooth gear 80 fixed to the casing 33 of the light source apparatus 30 (The phase difference motor M2 is provided with a drive shaft 75 and a drive gear 73). An endless timing belt B is installed in a tensioned state on external teeth 74 having the same pitch and provided on the entire outer peripheral surface of the drive gear 73 and external teeth 82 of the internal/external tooth gear 80. A plurality of inner peripheral teeth B1 of the endless timing belt B are in mesh with the external teeth 82 and the external teeth 74 (the pitch of the inner peripheral teeth B1 is the same as that of the external teeth 82 and the external teeth 74). Accordingly, the drive gear 73 (external teeth 74) and the internal/external tooth gear 80 (external 82) are interconnected via the endless timing belt B.

Figure 5:
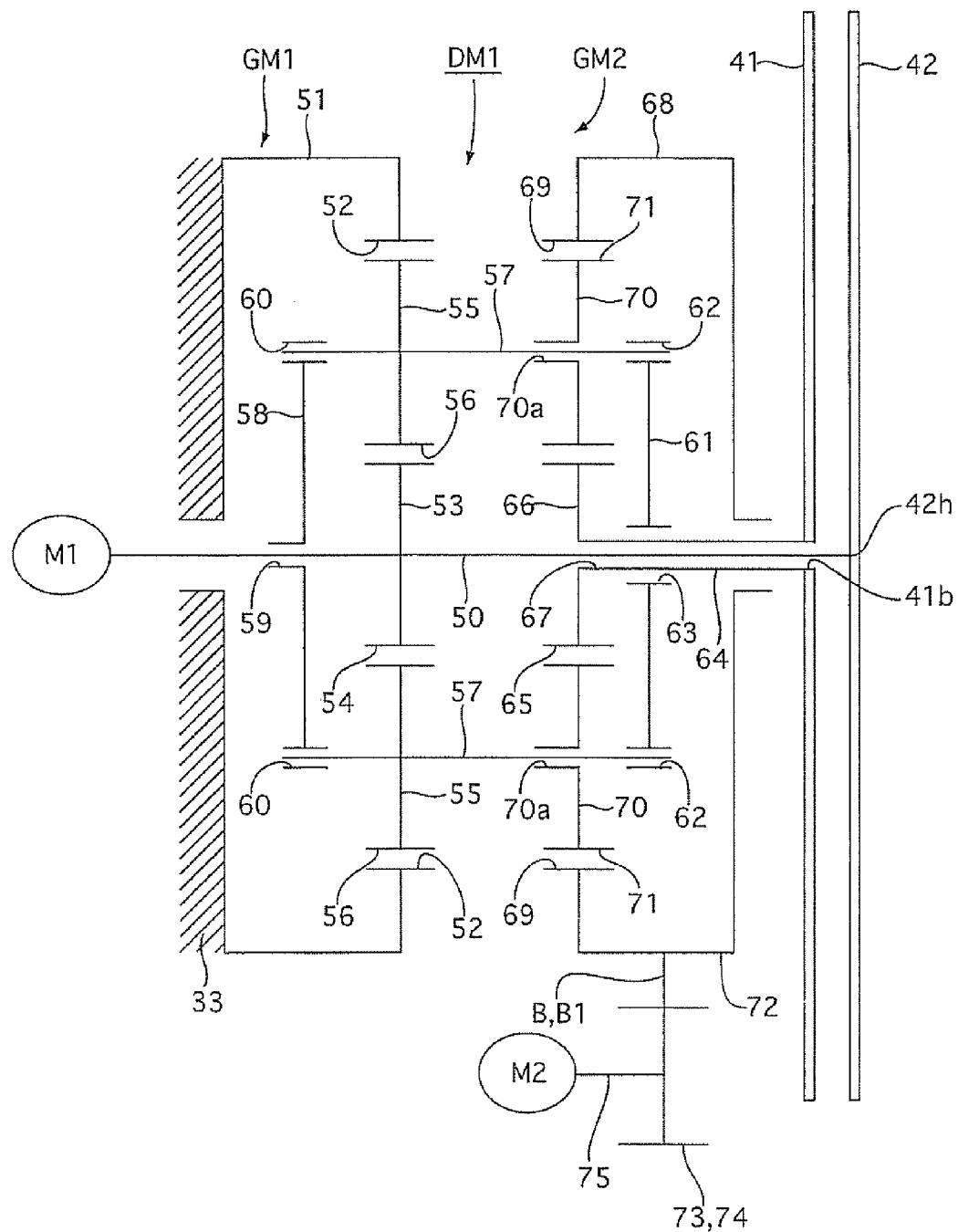
FIG. 5 is a schematic diagram of the drive mechanism shown in FIG. 4 and elements on the periphery thereof.

The internal tooth gear 83 has a diameter identical to the diameter of the internal/external tooth gear 68 shown in FIGS. 4 and 5 of the first embodiment. The internal tooth gear 83 is provided on its inner peripheral surface with internal teeth 84 identical to the internal teeth 69 of the internal/external tooth gear 68 and coaxial with the second sun gear 66. The internal tooth gear 83 is secured to the casing 33 of the light source apparatus 30 and is therefore non-rotatable. The internal tooth gear 83 is hatched in FIG. 6 to indicate that it is a stationary member.

In the second embodiment of the light source apparatus, the internal/external tooth gear 80, the first sun gear 53, and the first planet gears 55 constitute the first planetary gear mechanism GM1, and the second sun gear 66, the internal/external tooth gear 83 and the second planet gears 70 constitute the second planetary gear mechanism GM2.

The rotating actions of the first aperture controlling rotary plate 41 and the second aperture controlling rotary plate 42 will be discussed hereinafter.

Firstly, the following explanation will be applied to the case when the automatic light control switch S1 is turned ON.

When the controller 35 drives the chopper motor M1 in accordance with the brightness signal supplied from the CCD 16, the rotation of the chopper motor M1 is transferred to the second sun gear 66 through the same route as that in the first embodiment of the light source apparatus, so that the first sun gear 53, the second sun gear 66 and the second aperture controlling rotary plate 42 all rotate at the speed SP1. If the controller 35 drives the phase difference motor M2 in the same direction as the chopper motor M1 in accordance with the brightness signal supplied from the CCD 16, the internal/external tooth gear 80 rotates in a direction opposite to the rotation direction of each first planet gear 55, so that the rotation speed and the revolving speed of the first planet gears 55 increase. As a result, the first sun gear 53 and the drive shaft 50 rotate at the rotation speed SP2 that is higher than the rotation speed SP1 of the second sun gear 66. Thereupon, a difference in rotation speed is produced between the first aperture controlling rotary plate 41 and the second aperture controlling rotary plate 42, which varies the opening angle θ of each opening portion 40c and 40d in the range of 0 to 90 degrees, so that the quantity of illuminating light to be transmitted through the rotary shutter 40 is automatically changed to provide a desired brightness of the viewing site.

On the other hand, if the controller 35 rotates the phase difference motor M2 in the opposite direction to that of the chopper motor M1 in accordance with the brightness signal supplied from the CCD 16, the rotation direction of the internal/external tooth gear 80 becomes identical to the rotation direction of each first planet gear 55, so that the rotating speed and the revolving speed of the first planet gears 55 become lower than when the phase difference motor M2 is stopped. Consequently, the rotation speed SP3 of the first sun gear 53 and the drive shaft 50 becomes lower than the rotation speed SP1. Thereupon, a difference in rotation speed is produced between the first aperture controlling rotary plate 41 and the second aperture controlling rotary plate 42, which varies the opening angle θ of the opening portions 40c and 40d in the range of 0 to 90 degrees, so that the quantity of illuminating light to be transmitted through the rotary shutter 40 is automatically changed to provide a desired brightness to the viewing site.

In the second embodiment of the light source apparatus, the manual light control can also be carried out if the chopper motor control button S2 and the phase difference motor control button S3 are operated in a state where the automatic light control switch S1 is OFF.

The chopper motor control button S2 and the phase difference motor control button S3 are manually operated to rotate the chopper motor M1 and the phase difference motor M2. Upon the opening angle θ of each opening portion 40c and 40d becoming a desired value, the phase difference motor control button S3 is operated to stop the phase difference motor M2. Thereafter, the first sun gear 53 is rotated only by the chopper motor M1. If the phase difference motor M2 is stopped in this manner to stop the internal/external tooth gear 80 so that the drive mechanism DM2 operates only by the drive force of the chopper motor M1, the first sun gear 53 and the second sun gear 66 rotate in the same direction at the same rotation speed SP1, and the first aperture controlling rotary plate 41 and the second aperture controlling rotary plate 42 rotate in the same direction while maintaining the desired opening angle θ. Accordingly, an operator (user) can freely manually adjust the quantity of illuminating light to be transmitted to the light guide 20.

In the second embodiment of the light source apparatus, since the stationary bearing AS functions as a bearing for the cylindrical fitting portion 80a of the internal/external tooth gear 80, the weight of the internal/external tooth gear 80 is not applied to the drive shaft 50. Therefore, the load applied to the drive shaft 50 or the chopper motor M1 can be reduced in comparison with the drive mechanism DM1 in the first embodiment of the light source apparatus in which the weight of the internal/external tooth gear 68 is applied to the drive shaft 50 through the second planet gears 70.

Although the present invention has been discussed above with reference to each of the above described first and second embodiments of the light source apparatuses, the present invention is not limited to these embodiments and can be modified without departing from the spirit of the present invention.

For instance, in the first embodiment of the light source apparatus, the internal/external tooth gear 68 may be substantially in the form of a cylinder similar to the internal/external tooth gear 80 in the second embodiment, so that the cylindrical fitting portion thereof (corresponding to the cylindrical fitting portion 80a) can be rotatably supported by the rotary cylinder 64. In this alternative, the weight of the internal/external tooth gear 68 is not applied to the drive shaft 50 through the second planet gears 70, and hence, the load applied to the drive shaft 50 or the chopper motor M1 can be reduced.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A light source apparatus for an electronic endoscope comprising:
    a light source;
    a rotary shutter, having a rotation axis, which includes a pair of coaxial aperture controlling rotary plates, wherein an amount of light emitted from said light source toward a light guide is controlled by varying a relative rotation angle of said pair of aperture controlling rotary plates;
    a first planetary gear mechanism including a first internal tooth gear, which is a fixed gear and is coaxial with said rotation axis of said rotary shutter, a first sun gear which is rotated together with one of said pair of aperture controlling rotary plates via a motor and is coaxial with an axis of said first internal tooth gear, and at least one first planet gear which is simultaneously engaged with said first internal tooth gear and said first sun gear;
    a second planetary gear mechanism including a second internal tooth gear identical to said first internal tooth gear and coaxial with said rotation axis of said rotary shutter, a second sun gear which rotates together with the other of said pair of aperture controlling rotary plates and is identical to said first sun gear and coaxial with an axis of said second internal tooth gear, and at least one second planet gear, identical to said first planet gear, which is simultaneously engaged with said second internal tooth gear and said second sun gear; and
    a carrier device which is rotatable about an axis coincident with said rotation axis of said rotary shutter, wherein said carrier device holds said first and second planet gears in a same phase position with respect to said first and second internal tooth gears, and supports said first and second planet gears to allow said first and second planet gears to rotate relative to each other,
    wherein an endless timing belt, formed from a resilient material, is installed on an output gear which is fixed to a drive shaft of a phase-difference motor which is provided separate from said motor and an input tooth portion formed on an outer peripheral surface of said second internal tooth gear, and
    wherein said timing belt includes a meshing portion formed on an inner peripheral surface thereof, said meshing portion being engaged with said input tooth portion of said second internal tooth gear and said output gear.

2. An electronic endoscope having said light source apparatus according to claim 1, further comprising:
    an operating portion; and
    an insertion portion extending from said operating portion and inserted into an object to be viewed,
    wherein said light guide is inserted in said operating portion and said insertion portion so that a distal end of said light guide extends to a distal end of said insertion portion, and
    wherein said light source emits illuminating light to said light guide.

3. A light source apparatus for an electronic endoscope comprising:
    a light source;
    a rotary shutter, having a rotation axis, which includes a pair of coaxial aperture controlling rotary plates, wherein an amount of light emitted from said light source toward a light guide is controlled by varying a relative rotation angle of said pair of aperture controlling rotary plates;
    a first planetary gear mechanism including a first internal tooth gear, which is coaxial with said rotation axis of said rotary shutter, a first sun gear which is driven to rotate together with one of said pair of aperture controlling rotary plates via a motor and is coaxial with an axis of said first internal tooth gear, and at least one first planet gear which is simultaneously engaged with said first internal tooth gear and said first sun gear;
    a second planetary gear mechanism including a second internal tooth gear, which is a fixed gear, identical to said first internal tooth gear and coaxial with said rotation axis of said rotary shutter, a second sun gear which rotates together with the other of said pair of aperture controlling rotary plates and is identical to said first sun gear and coaxial with an axis of said second internal tooth gear, and at least one second planet gear, identical to said first planet gear, which is simultaneously engaged with said second internal tooth gear and said second sun gear; and a carrier device which is rotatable about an axis coincident with said rotation axis of said rotary shutter, wherein said carrier device holds said first and second planet gears in a same phase position with respect to said first and second internal tooth gears, and supports said first and second planet gears to allow said first and second planet gears to rotate relative to each other, wherein an endless timing belt, formed from a resilient material, is installed on an output gear which is fixed to a drive shaft of a phase-difference motor which is provided separate from said motor and an input tooth portion formed on an outer peripheral surface of said first internal tooth gear, and wherein said timing belt includes a meshing portion formed on an inner peripheral surface thereof, said meshing portion being engaged with said input tooth portion of said second internal tooth gear and said output gear.

4. The light source apparatus according to claim 3, wherein said first internal tooth gear is rotatably supported by a gear bearing.

5. An electronic endoscope having said light source apparatus according to claim 3, further comprising:

an operating portion; and an insertion portion extending from said operating portion and inserted into an object to be viewed, wherein said light guide is inserted in said operating portion and said insertion portion so that a distal end of said light guide extends to a distal end of said insertion portion, and wherein said light source emits illuminating light to said light guide.

* * * * *